US006548535B2

(12) United States Patent
Garcia et al.

(10) Patent No.: US 6,548,535 B2
(45) Date of Patent: Apr. 15, 2003

(54) METHOD FOR TREATING OCULAR HYPERTENSION

(75) Inventors: Maria L. Garcia, Edison, NJ (US); Gregory J. Kaczorowski, Edison, NJ (US); Owen B. McManus, Skillman, NJ (US)

(73) Assignee: Merck & Co., Inc., Rahway, NJ (US)

( * ) Notice: Subject to any disclaimer, the term of this patent is extended or adjusted under 35 U.S.C. 154(b) by 24 days.

(21) Appl. No.: 09/765,716

(22) Filed: Jan. 17, 2001

(65) Prior Publication Data

US 2001/0047025 A1 Nov. 29, 2001

Related U.S. Application Data

(60) Provisional application No. 60/176,694, filed on Jan. 18, 2000.

(51) Int. Cl.⁷ ...................... A61K 31/335; A61K 31/35
(52) U.S. Cl. ...................... 514/452; 514/453; 514/913
(58) Field of Search .................... 514/169, 170, 514/172, 452, 453, 913

(56) References Cited

U.S. PATENT DOCUMENTS

| 4,386,098 A | 5/1983 | Woltersdorf, Jr. et al. |
|---|---|---|
| 4,416,890 A | 11/1983 | Woltersdorf, Jr. |
| 4,426,388 A | 1/1984 | Woltersdorf, Jr. |
| 4,599,353 A | 7/1986 | Bito |
| 4,668,697 A | 5/1987 | Shepard et al. |
| 4,797,413 A | 1/1989 | Baldwin et al. |
| 4,824,857 A | 4/1989 | Goh et al. |
| 4,863,922 A | 9/1989 | Baldwin et al. |
| 4,883,819 A | 11/1989 | Bito |
| 5,001,153 A | 3/1991 | Ueno et al. |
| 5,153,192 A | 10/1992 | Dean et al. |
| 5,240,923 A | 8/1993 | Dean et al. |
| 5,378,703 A | 1/1995 | Dean et al. |
| 5,573,758 A | 11/1996 | Adorante et al. |
| 5,925,342 A | 7/1999 | Adorante et al. |

FOREIGN PATENT DOCUMENTS

| WO | WO 89/10757 | 11/1989 |
|---|---|---|
| WO | WO 94/28900 | 12/1994 |
| WO | WO 96/33719 | 10/1996 |

OTHER PUBLICATIONS

Invest. Ophthalmol. Vis. Sci., 38, 1997.
Arch. Ophthalmol., vol. 112, Jan. 1994, pp. 37–44.
Invest. Ophthalmol. & Vis. Sci., 32, 5, Apr. 1991, pp. 1593–1599.
P. Martin–Vasallo, et al., J Cell. Physiol., vol. 141, No. 2, 1989, pp. 243–252.
W. Grams, Cephalosporium–artige S Chimmelpilze, Hyphomycetes, pp. 38–140, 1971.

*Primary Examiner*—Zohreh Fay
(74) *Attorney, Agent, or Firm*—Sylvia A. Ayler; Mark R. Daniel; Valerie J. Camara

(57) ABSTRACT

This invention relates to the use of potent potassium channel blockers or a formulation thereof in the treatment of glaucoma and other conditions related to elevated intraocular pressure in the eye of a patient. This invention also relates to the use of such compounds to provide a neuroprotective effect to the eye of a mammalian species, particularly humans.

4 Claims, No Drawings

METHOD FOR TREATING OCULAR HYPERTENSION

This application claims benefit of No. 60/176,694, filed Jan. 18, 2000.

BACKGROUND OF THE INVENTION

Glaucoma is a degenerative disease of the eye wherein the intraocular pressure is too high to permit normal eye function. Damage eventually occurs to the optic nerve head, resulting in irreversible loss of visual function. If untreated, glaucoma may eventually lead to blindness. Elevated intraocular pressure or ocular hypertension, is now believed by the majority of ophthalmologists to represent the earliest phase in the onset of glaucoma.

Many of the drugs formerly used to treat glaucoma proved unsatisfactory. The early methods of treating glaucoma employed pilocarpine and produced undesirable local effects that made this drug, though valuable, unsatisfactory as a first line drug. More recently, clinicians have noted that many β-adrenergic antagonists are effective in reducing intraocular pressure. While many of these agents are effective for this purpose, there exist some patients with whom this treatment is not effective or not sufficiently effective. Many of these agents also have other characteristics, e.g., membrane stabilizing activity, that become more apparent with increased doses and render them unacceptable for chronic ocular use and can also cause cardiovascular effects.

Although pilocarpine and β-adrenergic antagonists reduce intraocular pressure, none of these drugs manifests its action by inhibiting the enzyme carbonic anhydrase, and thus they do not take advantage of reducing the contribution to aqueous humor formation made by the carbonic anhydrase pathway.

Agents referred to as carbonic anhydrase inhibitors decrease the formation of aqueous humor by inhibiting the enzyme carbonic anhydrase. While such carbonic anhydrase inhibitors are now used to treat intraocular pressure by systemic and topical routes, current therapies using these agents, particularly those using systemic routes are still not without undesirable effects. Because carbonic anhydrase inhibitors have a profound effect in altering basic physiological processes, the avoidance of a systemic route of administration serves to diminish, if not entirely eliminate, those side effects caused by inhibition of carbonic anhydrase such as metabolic acidosis, vomiting, numbness, tingling, general malaise and the like. Topically effective carbonic anhydrase inhibitors are disclosed in U.S. Pat. Nos. 4,386,098; 4,416,890; 4,426,388; 4,668,697; 4,863,922; 4,797,413; 5,378,703, 5,240,923 and 5,153,192.

Prostaglandins and prostaglandin derivatives are also known to lower intraocular pressure. U.S. Pat. No. 4,883,819 to Bito describes the use and synthesis of PGAs, PGBs and PGCs in reducing intraocular pressure. U.S. Pat. No. 4,824,857 to Goh et al. describes the use and synthesis of PGD2 and derivatives thereof in lowering intraocular pressure including derivatives wherein C-10 is replaced with nitrogen. U.S. Pat. No. 5,001,153 to Ueno et al. describes the use and synthesis of 13,14-dihydro-15-keto prostaglandins and prostaglandin derivatives to lower intraocular pressure. U.S. Pat. No. 4,599,353 describes the use of eicosanoids and eicosanoid derivatives including prostaglandins and prostaglandin inhibitors in lowering intraocular pressure.

Prostaglandin and prostaglandin derivatives lower intraocular pressure by increasing uveoscleral outflow. This is true for both the F type and A type of Pgs and hence presumably also for the B, C, D, E and J types of prostaglandins and derivatives thereof. A problem with using prostaglandin derivatives to lower intraocular pressure is that these compounds often induce an initial increase in intraocular pressure, can change the color of eye pigmentation and cause proliferation of some tissues surrounding the eye.

As can be seen, there are several current therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and ocular hypertension (elevated intraocular pressure) using indole diterpene compounds having the structural formula I:

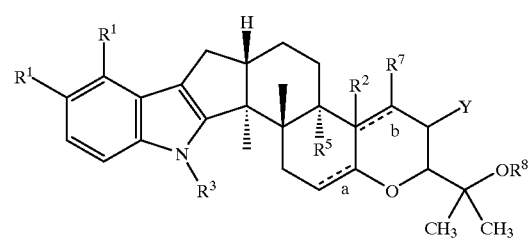

(I)

or a pharmaceutically acceptable salt, enantiomer, diastereomer or mixture thereof.

DETAILED DESCRIPTION OF THE INVENTION

The present invention is directed to a method for treating ocular hypertension or glaucoma which comprises administering to a patient in need of such treatment a therapeutically effective amount of a compound of Formula I:

(I)

or a pharmaceutically acceptable salt, enantiomer, diastereomer or mixture thereof: wherein, $R^1$ is:

(a) H, (b)

$$\text{CH}_3\text{-C(CH}_3\text{)=CH-CH}_2\text{-}$$

or (c) epoxide with two CH$_3$ groups;

$R^2$ is:
(a) $CO_2C_{1-6}$alkyl,
(b) H,
(c) OH, or
$R^2$ and $R^7$ are taken together to form an oxirane ring when b is a single bond;

$R^3$ is:
(a) H, or
(b) (C=O)O$C_{1-6}$alkyl;

$R^5$ is:
(a) H,
(b) OH, or
(c) O$C_{1-6}$alkyl;

$R^7$ is H, O$C_{1-6}$ alkyl or $R^7$ and $R^2$ are taken together to form an oxirane ring when b is a single bond;

Y is:
(a) H,
(b) OH,
(c) O$C_{1-6}$alkyl,
or Y and $R^8$ are joined such that one of the following rings is formed:

(1)

(2)

$R^8$ is $C_{1-10}$ alkyl or $C_{2-10}$ alkenyl; and
_____ is a double bond optionally present at a or b or at both a and b.

Another embodiment of the invention is the method described above wherein the compound of formula I is applied as a topical formulation.

Yet another embodiment is a method for treating ocular hypertension or glaucoma which comprises administering to a patient in need of such treatment a therapeutically effective amount of a compound selected from:

(a)

(b)

(c)

(d)

(e)

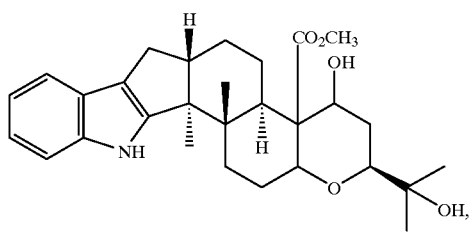

(f)

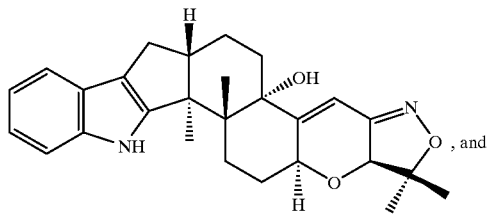
, and (g)

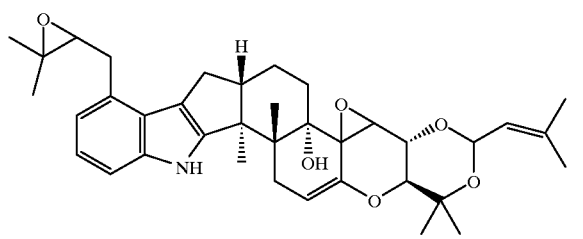

and pharmaceutically acceptable salts, enantiomers, diastereomers and mixtures thereof.

Yet another embodiment contemplates the method described above wherein the topical formulation is a solution or suspension.

And yet another embodiment is the method described above, which comprises administering a second active ingredient, concurrently or consecutively, wherein the second active ingredient is selected from β-adrenergic blocking agent, a parasympathomimetic agent, a carbonic anhydrase inhibitor, and a prostaglandin or a prostaglandin derivative.

Another embodiment is the method described above wherein the β-adrenergic blocking agent is timolol; the parasympathomimetic agent is pilocarpine; the carbonic anhydrase inhibitor is dorzolamide, acetazolamide, metazolamide or brinzolamide; the prostaglandin is latanoprost or rescula, and the prostaglandin derivative is a hypotensive lipid derived from PGF2α prostaglandins.

A further embodiment is a method for treating macular edema or macular degeneration which comprises administering to a patient in need of such treatment a pharmaceutically effective amount of a compound of structural formula I:

(I)

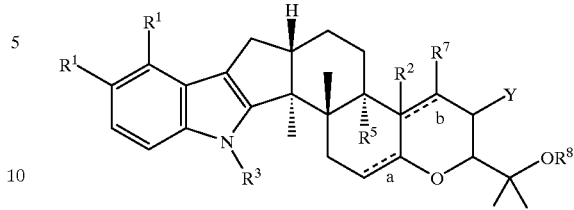

or a pharmaceutically acceptable salt, enantiomer, diastereomer or mixture thereof: wherein, $R^1$ is:

(a)

H, (b)

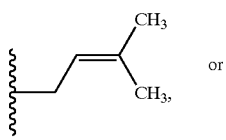
or (c)

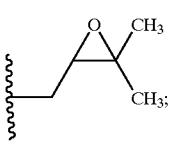

$R^2$ is:
(a) $CO_2C_{1-6}$alkyl,
(b) H,
(c) OH, or
$R^2$ and $R^7$ are taken together to form an oxirane ring when b is a single bond;

$R^3$ is:
(a) H, or
(b) (C=O)O$C_{1-6}$alkyl;

$R^5$ is:
(a) H,
(b) OH, or
(c) $OC_{1-6}$alkyl;

$R^7$ is H, $OC_{1-6}$ alkyl or $R^7$ and $R^2$ are taken together to form an oxirane ring when b is a single bond;

Y is:
(a) H,
(b) OH,
(c) $OC_{1-6}$alkyl,
or Y and $R^8$ are joined such that one of the following rings is formed:

(1)

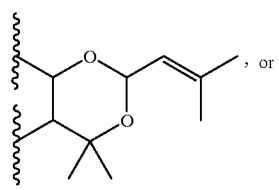
, or (2)

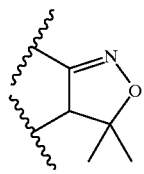

$R^8$ is $C_{1-10}$ alkyl or $C_{2-10}$ alkenyl; and

——— is a double bond optionally present at a or b or at both a and b.

Another embodiment is the method described above wherein the compound of formula I is applied as a topical formulation.

Yet another embodiment is a method for treating macular edema or macular degeneration which comprises administering to a patient in need of such treatment a pharmaceutically effective amount of a compound selected from:

(a)

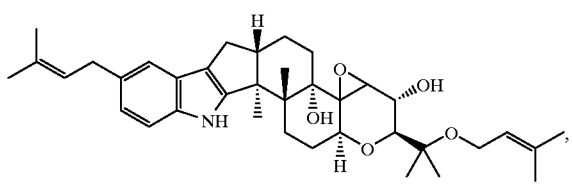

(b)

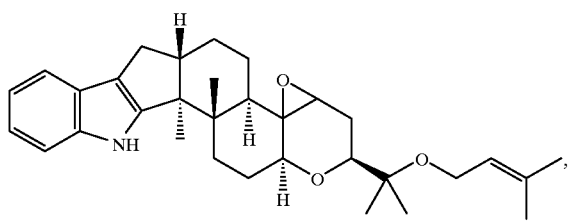

(c)

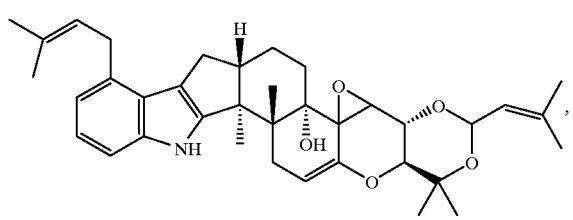

(d)

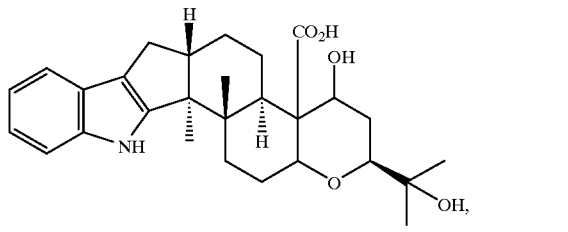

(e)

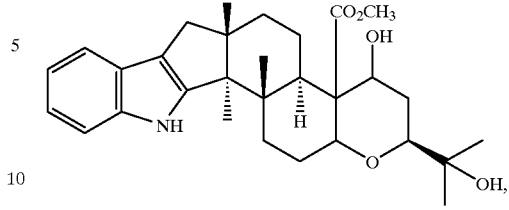

(f)

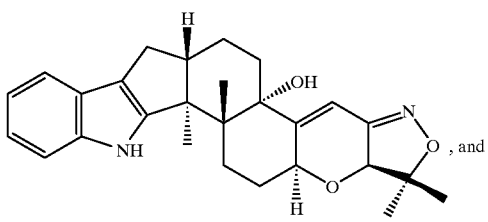

, and (g)

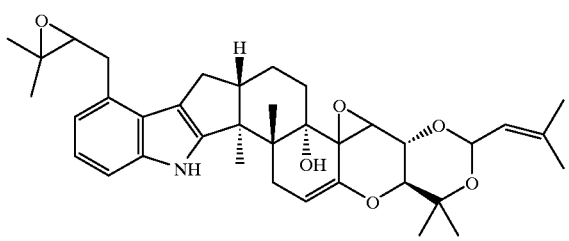

and pharmaceutically acceptable salts, enantiomers, diastereomers and mixtures thereof.

A further embodiment is illustrated by a method for increasing retinal and optic nerve head blood velocity or increasing retinal and optic nerve oxygen tension which comprises administering to a patient in need of such treatment a therapeutically effective amount of a compound of Formula I:

(I)

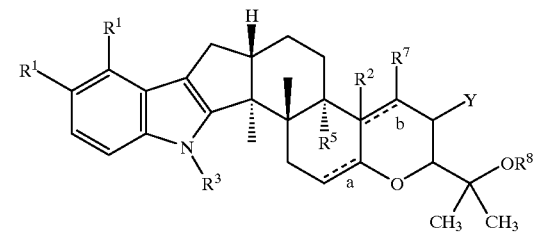

or a pharmaceutically acceptable salt, enantiomer, diastereomer or mixture thereof: wherein, $R^1$ is:

(a) H, (b)

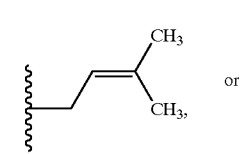 or

-continued (c) 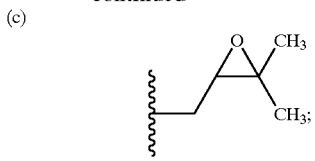

R² is:
(a) CO₂C₁₋₆alkyl,
(b) H,
(c) OH, or
R² and R⁷ are taken together to form an oxirane ring when b is a single bond;

R³ is:
(a) H, or
(b) (C=O)OC₁₋₆alkyl;

R⁵ is:
(a) H,
(b) OH, or
(c) OC₁₋₆alkyl;

R⁷ is H, OC₁₋₆ alkyl or R⁷ and R² are taken together to form an oxirane ring when b is a single bond;

Y is:
(a) H,
(b) OH,
(c) OC₁₋₆alkyl,
or Y and R⁸ are joined such that one of the following rings is formed:

(1) 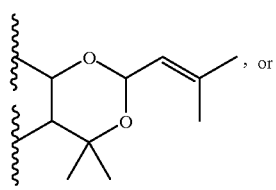, or (2) 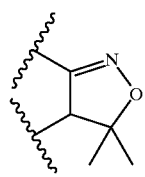

R⁸ is C₁₋₁₀ alkyl or C₂₋₁₀ alkenyl; and
_____ is a double bond optionally present at a or b or at both a and b.

And another embodiment is the method described above wherein the compound of formula I is applied as a topical formulation.

And still a further embodiment is a method for increasing retinal and optic nerve head blood velocity or increasing retinal and optic nerve oxygen tension which comprises administering to a patient in need of such treatment a therapeutically effective amount of a compound selected from:

(a) 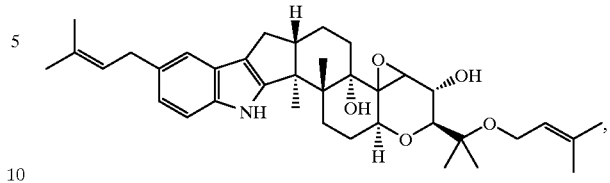

(b) 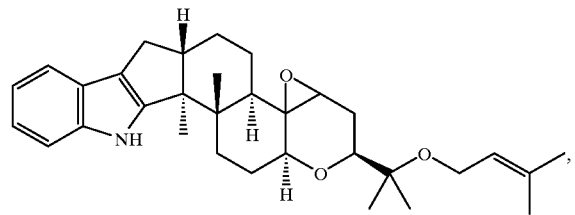

(c) 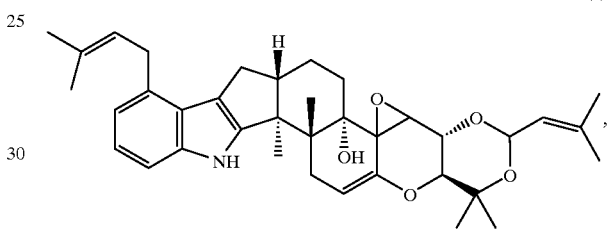

(d) 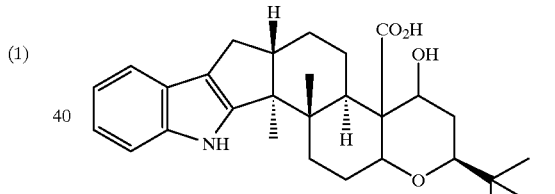

(e) 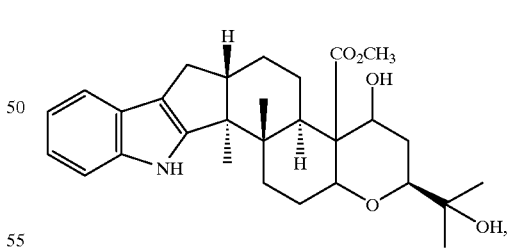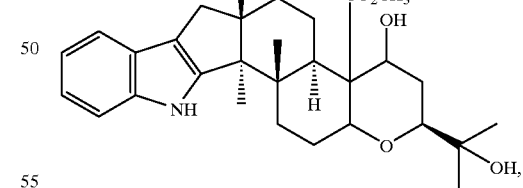

(f) 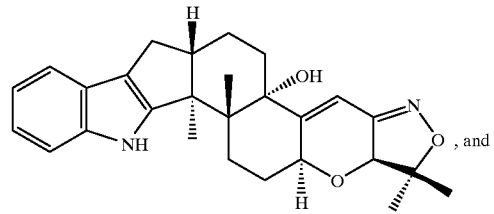, and

-continued (g)

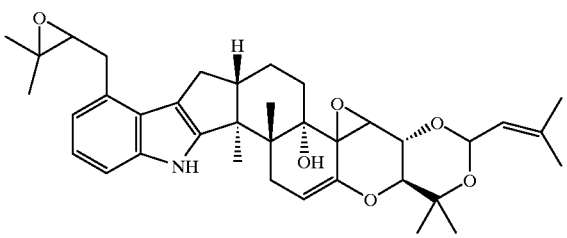

and pharmaceutically acceptable salts, enantiomers, diastereomers and mixtures thereof.

Another embodiment of the invention is a method for providing a neuroprotective effect to a mammalian eye which comprises administering to a patient in need of such treatment a therapeutically effective amount of a compound of Formula I:

(I)

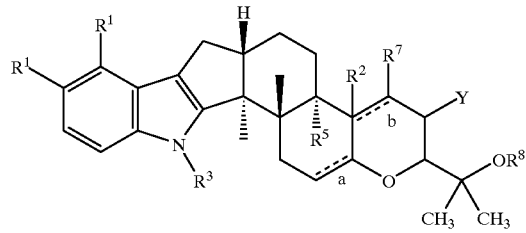

or a pharmaceutically acceptable salt, enantiomer, diastereomer or mixture thereof: wherein, $R^1$ is:

(a) H, (b) 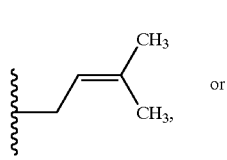 or (c) 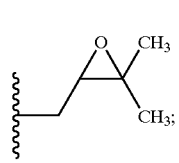

$R^2$ is:

(a) $CO_2C_{1-6}$alkyl,
(b) H,
(c) OH, or
$R^2$ and $R^7$ are taken together to form an oxirane ring when b is a single bond;

$R^3$ is:

(a) H, or
(b) (C=O)$OC_{1-6}$alkyl;

$R^5$ is:

(a) H,
(b) OH, or
(c) $OC_{1-6}$alkyl;

$R^7$ is H, $OC_{1-6}$ alkyl or $R^7$ and $R^2$ are taken together to form an oxirane ring when b is a single bond;

Y is:

(a) H,
(b) OH,
(c) $OC_{1-6}$alkyl, or Y and $R^8$ are joined such that one of the following rings is formed:

(1)

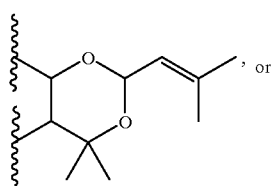 , or (2)

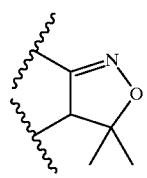

$R^8$ is $C_{1-10}$ alkyl or $C_{2-10}$ alkenyl; and

──── is a double bond optionally present at a or b or at both a and b.

Also within the scope of the invention is the method described above wherein the compound of Formula I is applied as a topical formulation.

Another embodiment is represented by a method for providing a neuroprotective effect to a mammalian eye which comprises administering to a patient in need of such treatment a therapeutically effective amount of a compound selected from:

(a)

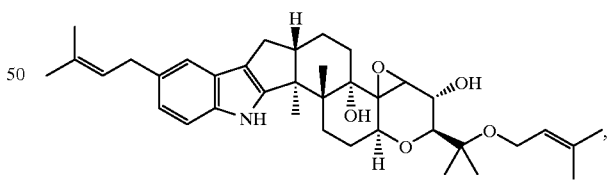

(b)

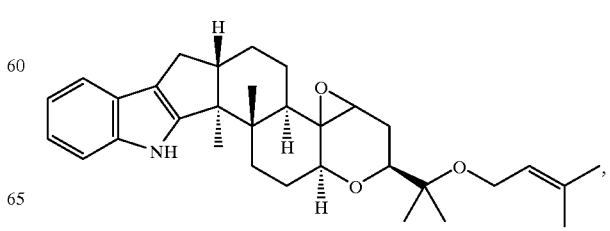

(c)
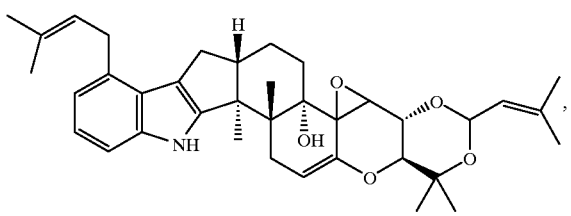

(d)
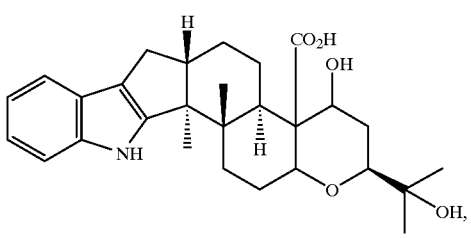

(e)
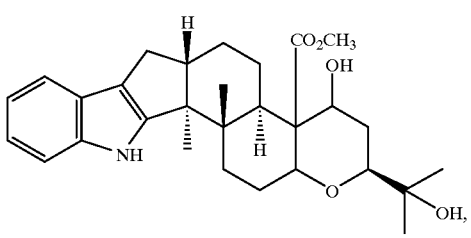

(f)
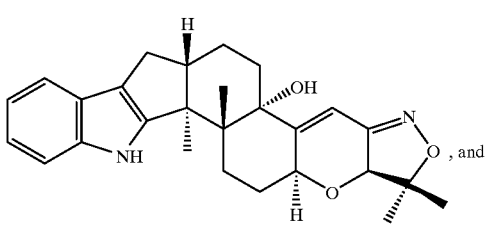, and (g)
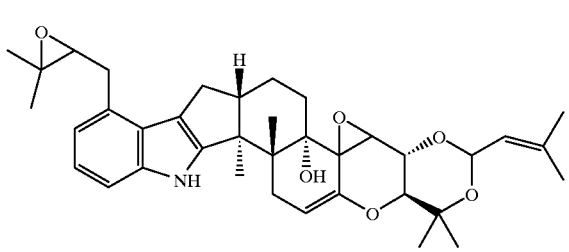

and pharmaceutically acceptable salts, enantiomers, diastereomers and mixtures thereof.

Also contemplated to be within the scope of the present invention is the topical formulation of Compound I as described above wherein the topical formulation also contains xanthan gum or gellan gum.

The invention is described herein in detail using the terms defined below unless otherwise specified.

When any variable (e.g., aryl, alkyl, $R^1$, $R^2$, etc.) occurs more than one time in any constituent or in a structural formula, its definition on each occurrence is independent of its definition at every occurrence. Also, combinations of substituents and/or variables are permissible only if such combinations result in stable compounds.

Also included within the scope of this invention are pharmaceutically acceptable salts or esters, where a basic or acidic group is present in a compound of Formula I, such as, for example on the substituted alkyl moiety. When an acidic substituent is present, i.e. —COOH, there can be formed the ammonium, sodium, or calcium salt, and the like, for use as the dosage form. Also, in the case of the —COOH group being present, pharmaceutically acceptable esters may be employed, e.g., acetate, maleate, pivaloyloxymethyl, and the like, and those esters known in the art for modifying solubility or hydrolysis characteristics for use as sustained release or prodrug formulations.

Where a basic group is present, such as amino, acidic salts such as hydrochloride, hydrobromide, acetate, pamoate and the like may be used as the dosage form.

As used herein "alkyl" is intended to include both branched- and straight-chain saturated aliphatic hydrocarbon groups having the specified number of carbon atoms and includes methyl (Me), ethyl (Et), propyl (Pr), butyl (Bu), pentyl, hexyl and the like. "Alkoxy" represents an alkyl group of the indicated number of carbon atoms attached through an oxygen bridge. "Cycloalkyl" is intended to include saturated carbon ring groups such as cyclopropyl, cyclobutyl, cyclopentyl, and cyclohexyl (Cyh). "Alkenyl" is intended to include hydrocarbon groups of either a straight or branched configuration with one or more carbon—carbon double bonds which may occur in any stable point along the chain, such as ethenyl, propenyl, butenyl, and the like. "Alkynyl" is intended to include hydrocarbon groups of either a straight or branched configuration with one or more carbon—carbon triple bonds which may occur in any stable point along the chain, such as ethynyl, propynyl, butynyl, and the like. "Halo" or "halogen" as used herein means fluoro, chloro, bromo and iodo. The term "Boc" refers to t-butyloxy-carbonyl.

This invention is also concerned with a method of treating ocular hypertension or glaucoma by administering to a patient in need thereof one of the compounds of formula I in combination with a β-adrenergic blocking agent such as timolol, a parasympathomimetic agent such as pilocarpine, carbonic anhydrase inhibitor such as dorzolamide, acetazolamide, metazolamide or brinzolamide, a prostaglandin such as latanoprost, rescula, S1033 or a prostaglandin derivative such as a hypotensive lipid derived from PGF2α prostaglandins. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2α}$ 1-$OCH_3$), or a hydroxy group ($PGF_{2α}$ 1-OH).

Preferred potassium channel blockers are calcium activated potassium channel blockers. More preferred potassium channel blockers are high conductance, calcium activated potassium (maxi-K) channel blockers. Maxi-K channels are a family of ion channels that are prevalent in neuronal, smooth muscle and epithelial tissues and which are gated by membrane potential and intracellular $Ca^{2+}$.

Intraocular pressure (IOP) is controlled by aqueous humor dynamics. Aqueous humor is produced at the level of the non-pigmented ciliary epithelium and is cleared primarily via outflow through the trabecular meshwork. Aqueous humor inflow is controlled by ion transport processes. It is thought that maxi-K channels in non-pigmented ciliary epithelial cells indirectly control chloride secretion by two mechanisms; these channels maintain a hyperpolarized membrane potential (interior negative) which provides a driving force for chloride efflux from the cell, and they also provide a counter ion ($K^+$) for chloride ion movement. Water moves passively with KCl allowing production of aqueous humor. Inhibition of maxi-K channels in this tissue would diminish inflow. Maxi-K channels have also been shown to control the contractility of certain smooth muscle tissues, and, in some cases, channel blockers can contract quiescent muscle, or increase the myogenic activity of spontaneously active tissue. Contraction of ciliary muscle would open the trabecular meshwork and stimulate aqueous humor outflow, as occurs with pilocarpine. Therefore maxi-K channels could profoundly influence aqueous humor dynamics in several ways; blocking this channel would decrease IOP by affecting inflow or outflow processes or by a combination of affecting both inflow/outflow processes.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering of IOP promotes increased blood flow to the retina and optic nerve. Accordingly, this invention relates to a method for treating macular edema, macular degeneration or a combination thereof.

Additionally, macular edema is swelling within the retina within the critically important central visual zone at the posterior pole of the eye. An accumulation of fluid within the retina tends to detach the neural elements from one another and from their local blood supply, creating a dormancy of visual function in the area.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37–44; Investigative Ophthamol. & Visual Science, 32, 5, April 1991, pp. 1593–99. It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof.

The maxi-K channel blockers used are preferably administered in the form of ophthalmic pharmaceutical compositions adapted for topical administration to the eye such as solutions, ointments, creams or as a solid insert. Formulations of this compound may contain from 0.01 to 5% and especially 0.5 to 2% of medicament. Higher dosages as, for example, about 10% or lower dosages can be employed provided the dose is effective in reducing intraocular pressure, treating glaucoma, increasing blood flow velocity or oxygen tension or providing a neuroprotective effect. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The maxi-K channel blockers used in the present invention are made by a microbiological processes employing the Culture Nalanthalama sp. (MF 5785). The process has been previously described in U.S. Pat. No. 5,541,208, herein incorporated by reference. This culture, ATCC 74192, is available from the American Type Culture Collection located at 12301 Parklawn Drive in Rockville, Md. Modified isoxazolines, such as alkyl esters, can be made by modifications of the fungal isolates via synthetic protocols known in the art.

The starting material for the fermentation may be selected from paxilline or any indole diterpene having a hydroxyl group beta to a carbonyl group. The diterpene alkaloid of the formula:

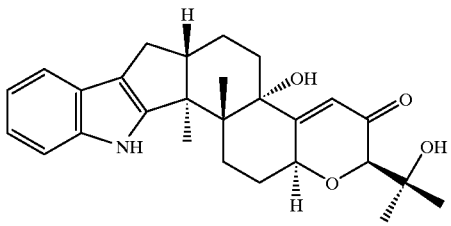

is known in the art as Paxilline and is produced from a number of microorganisms. Paxilline, and the related compounds paspalitrem and aflatrem are fungal metabolites known to be tremorgens. Paxilline or a related indole diterpene containing the necessary hydroxyl-carbonyl functionality may be reacted with hydroxylamine in a suitable solvent under appropriate conditions to form the oxime which is further reacted with tributylphosphine and diphenyldisulfide to produce an isoxazoline such as paxizoline. The claimed process is not limited to producing potassium channel antagonists such as paxizoline but may also be used to produce pharmaceutically active isoxazolines or drugs containing an isoxazoline ring. The scheme below indicates the required functionality and describes the general process:

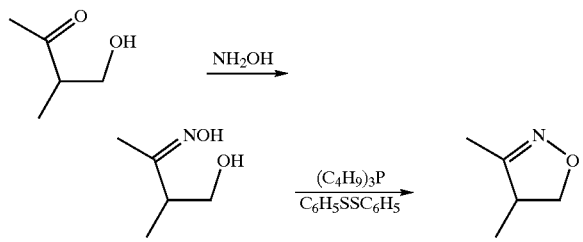

As shown above, the claimed process relates generally to the initial formation of an oxime which subsequently reacts with tributylphosphine and diphenyldisulfide to form the heterocycle isoxazoline or isoxazole.

The free acid groups on the compounds produced by the microbiological process may also be readily modified to the alkyl ester. For example, trimethylsilyldiazomethane added to a methanolic solution containing a free acid moiety is readily converted to the methyl ester. Other simple alkyl or aryl or benzyl esters may readily be prepared by conventional means to produce compounds within the scope of the present invention.

The indole nitrogen may readily be protected with a suitable protecting group selected from, for example, t-butyloxycarbonyl or other protecting group selected from groups described in "Protective Groups in Organic Synthesis" by Greene and Wutts (1991). Furthermore, the free alcohol moieties may also be protected using standard hydroxyl protecting groups.

The compounds used in the present invention can be made by a fermentation process for producing potassium channel antagonists comprising:

(a) inoculating seed medium (Table 1) with mycelia of Nalanthalama sp. MF5785 (ATCC 74192);
(b) incubating the inoculated mycelia at room temperature (20–30° C.) under humid conditions with constant fluorescent light, preferably with shaking, most preferably on a rotary shaker with a 5-cm throw at 220 rpm;
(c) using the culture produced in step (b) to inoculate a liquid production medium and further incubating under the conditions defined in step (b) to produce Compounds A, B, C, D and G.

Maximal accumulation of compounds A, B, C, D and G in the fermentation broth occurs between 7–11 days. The invention further comprises a step (d) in which the compounds produced in the fermentation broth under suitable defined and controlled conditions are purified and isolated from the broth. Suitable isolation procedures include, for example, extraction of the culture medium with an alcoholic or oxygenated solvent, such as an ether or ketone, preferably methylethylketone.

The strain MF5785 has been identified as an Nalanthaloma. The fungus was isolated from unidentified twigs collected in the province of Nuevo Leon, Mexico. The generic disposition is based the undifferentiated, unbranched, solitary, enteroblastic, phialidic conidiogenous cells that give rise to conidia that are small, subglobose, hyaline and smooth. Within the genus Acremonium, this isolate could be assigned to the series terricola because the conidia adhere to the conidogenous cells in dry chains. However, the isolate does not match any of the taxa in this series presented by Gams in his monograph of the genus Acremonium (W. Grams. 1971. *Cephalosporium-artige Schimmelpilze (Hyphomycetes)*. This organism grows well and sporulates abundantly in most mycological media. In agar culture, the strain exhibits the following morphological features:

Colonies growing moderately well on oatmeal agar (Difco Laboratories), 25° C., 12 hr photoperiod, after 21 days attaining 34–36 mm in diameter, slightly raised, velvety, finely cottony, becoming minutely granular at the center, dull, dry, faintly zonateith margin even and submerged, white at the margin becoming dull vinaceous to grayish vinaceous, Pale Vinaceous-Fawn, Vinaceous-Buff, Light Vinaceous-Fawn, to Vinaceous-Fawn (capitalized color names from Ridgway, R. 1912. *Color Standards and Nomenclature*, Washington, D.C.). Odors and exudates absent.

Colonies growing moderately fast on Emerson Yp Ss (Difco Laboratories) agar, 25° C., 12 hr photoperiod, after 21 days attaining 30 mm diameter, appressed to slightly raised, faintly radially sulcate, faintly zonate, velvety, with minute drops of watery exudate towards center, dry, dull, with margin submerged, minute fimbriate to wavy, translucent, white to pale vinaceous, Pale Vinaceous-Fawn, Light Vinaceous-Fawn, translucent to pale yellow in reverse. Odors and exudates absent.

Colonies growing moderately fast on Barnett's oak wilt agar (Barnett, H. L. 1953. Isolation and identification of the oak wilt fungus. West Virginia Agricultural Experiment Station Bulletin 359T: 1-15.), 25° C., 12 hr photoperiod, after 21 days attaining 25 mm diameter, appressed, pruinose to downy, farinaceous towards the center, radially rivulose, faintly zonate, with margin even and submerged, white to pale vinaceous, with farinaceous granules pale vinaceous gray. Granular texture caused by aggregation of conidiophores into small pustules and accumulations of dry conidia. Odors and exudates absent.

No growth occured at 37° C. on Emerson Yp Ss agar after 21 days.

Conidiophores micronematous, occasionally semi-micronematous, integrated, up to 30 μm tall, but usually 6–12 μm tall, branched or not, septate or not, often only a simple right-angle branch from main hyphal axis, usually with a single terminal conidiogenous locus, but occasionally conidiogenous loci are lateral or intercalary. Conidiogenous cells terminal or intercalary, appearing enteroblastic and phialidic, occasionally swollen at the base. Conidia hyaline, thin-walled, broadly ellipsoidal or obovate, with a slightly flattened base, 2–5×15.2.5 μm, accumulating in dry chains, sometime with faint connectives evident.

Hyphae septate, branched, finely incrusted in mature regions of the colonies.

In general, Compounds A, B, C, D and G can be produced by culturing (fermenting) strain MF5785, ATCC 74192, in an aqueous nutrient medium containing assimilable carbon and nitrogen sources, preferably under submerged aerobic conditions, and shaking the culture under constant fluorescent light, preferably 450 to 700 nm, until a substantial amount of Compounds A, B, C, D and G is detected in the fermentation broth. The culture is incubated in a aqueous medium at a temperature between 20° C. and 37° C., preferably 25° C. for a period of time necessary to complete the formation of Compounds A, B, C, D, and G, usually for a period between 3 to 28 days, preferably between 7 to 11 days, preferably on a shaking means, most preferably on a rotary shaker operating at 220 rpm with a 5 cm throw. The aqueous production medium is maintained at a pH between 5 and 8, preferably about 6.0, at the initiation and termination (harvest) of the fermentation process. The desired pH may be maintained by the use of a buffer such as [2-(N-morpholino)ethanesulfonic acid] monohydrate (MES), 3-(N-morpholino)propanesulfonic acid (MOPS), phosphate buffer or any other buffer effective in pH 5 to 8, or by choice of nutrient materials which inherently possess buffering properties, such as production media described herein below. The active compound is extracted from the mycelial growth of the culture is with a suitable solvent, such as alcoholic or oxygenated solvent such as an ester or ketone. The preferred solvent for extraction is methylethylketone (MEK). The solution containing the desired compound is concentrated and then subjected to chromatographic separation to isolate compounds A, B, C, D and G from the cultivation medium.

The preferred sources of carbon in the nutrient medium include sucrose, glucose, fructose, mannitol, glycerol, xylose, galactose, lactose, sorbitol, starch, dextrin, other sugars and sugar alcohols, starches and other carbohydrates, or carbohydrates derivatives, and the like. Other sources which may be included are maltose, rhamnose, raffinose, arabinose, mannose, salicin, sodium succinate, acetate, and the like as well as complex nutrients such as yellow corn meal, oat flour, millet, rice, cracked corn, and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium.

The preferred sources of nitrogen are yeast extract, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as methionine, phenylalanine, serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form because less pure materials which contain traces of growth factors and considerable quantities of mineral nutrients are also suitable for use. When desired, there may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0, and trace elements ranging from 0.001 to 0.1 percent by weight of the medium.

If necessary, especially when the culture medium foams seriously, a defoaming agent, such as polypropylene glycol 2000 (PPG-2000), liquid paraffin, fatty oil, plant oil, mineral oil or silicone may be added.

Submerged aerobic fermentation conditions in fermentors are preferred for the production of Compounds A, B, C, D and G in large amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Compounds A, B, C, D and G. Accordingly, it is desirable first to produce a vegetative inoculum of the organism by inoculating a relatively small quantity of culture medium with spores or mycelia of the organism produced in a "slant," or from previously prepared frozen mycelia, and culturing the inoculated medium, also called the "seed medium", and then aseptically transferring the cultured vegetative inoculum to large tanks. The seed medium, in which the inoculum is produced may be seen in Table 1 and is generally autoclaved to sterilize the medium prior to inoculation. The seed medium is generally adjusted to a pH between 5 and 8, preferably about 6.8, prior to the autoclaving step by suitable addition of an acid or base, preferably in the form of a dilute solution of hydrochloric acid or sodium hydroxide. Growth of the culture in this seed medium is maintained between 26° C. and 37° C., preferably 25° C. Incubation of culture MF5785 (ATCC 74192) in a seed medium, preferably that in Table 1, is usually conducted for a period of about 2 to 6 days, preferably 3 to 4 days, with shaking, preferably on a rotary shaker operating at 220 rpm with a 5 cm throw; the length of incubation time may be varied according to fermentation conditions and scales. If appropriate, a second stage seed fermentation may be carried out in the seed medium (Table 1) for greater production of mycelial mass by inoculating fresh seed medium with a portion of the culture growth and then incubating under similar conditions but for a shortened period. The resulting growth then may be employed to inoculate, a production medium, preferably the Liquid Production Medium (Table 2). The fermentation liquid production medium inoculated with the seed culture growth is incubated for 3 to 28 days, usually 7 to 11 days, with agitation. Agitation and aeration of the culture mixture may be accomplished in a variety of ways. Agitation may be provided by a propeller or similar mechanical agitation equipment, by revolving or shaking the fermentation mixture within the fermentor, by various pumping equipment or by the passage of sterile air through the medium. Aeration may be effected by passing sterile air through the fermentation mixture.

Preferred seed and production media for carrying out the fermentation include the following media:

TABLE 1

Seed Medium

| | per liter | Trace Element Mix | per liter |
|---|---|---|---|
| Corn Steep Liquor | 5 g | $FeSO_4.H_2O$ | 1 g |
| Tomato Paste | 40 g | $MnSO_4.4H_2O$ | 1 g |
| Oat flour | 10 g | $CuCl_2.2H_2O$ | 25 mg |
| Glucose | 10 g | $CaCl_2$ | 100 mg |
| Trace element mix | 10 mL | $H_3BO_3$ | 56 mg |
| | | $(NH_4)_6Mo_7O_{24}.4H_2O$ | 19 mg |
| pH = 6.8 | | $ZnSO_4.7H_2O$ | 200 mg |

TABLE 2

| Component | Liquid Production Medium Per Liter |
|---|---|
| Yellow Cornmeal | 50.0 g |
| Yeast Extract | 1.0 g |
| Sucrose | 80.0 g |
| Distilled Water | 1000.0 mL |

The following examples are provided to illustrate the present invention and should not be construed as limiting the scope of the invention.

EXAMPLE 1

Production of Compounds A, B, C, D and G

Step A: Fermentation Conditions for Production of Compounds A–D and G

Fermentation conditions for the production of Compounds A, B, C, D and G by the microorganism Nalanthamala sp. were as follows: vegetative mycelia of a culture of the above microorganism were prepared by inoculating 54 mL of seed medium (Table 1) in a 250 mL unbaffled Erlenmeyer flask with frozen mycelia of MF5785 (ATCC 74192). Seed flasks were incubated at 25° C. and 50% relative humidity on a rotary shaker with a 5-cm throw at 220 rpm in a room with constant fluorescent light, about 400 to 750 nm. Two-mL portions of the resulting 3-day culture were used to inoculate 50 mL portions of Liquid Production Medium (Table 2) in 250 mL unbaffled Erlenmeyer flasks; these cultures were incubated at 25° C., 220 rpm with 50% relative humidity in a room with constant fluorescent light. The products appeared in the fermentation as early as 7 days with maximal accumulation observed at day 11. At harvest, the compounds were extracted as described below.

Step B: Isolation of Compounds A, B, C, D and G

The fermentation broth of MF5785 (ATCC 74192), prepared above (3 L WBE; $IC_{50}$=10 μl WBE per mL in [$^{125}$I]ChTX binding assay (described in Example 5) was extracted with methyl ethyl ketone, and the solvent was removed in vacuo. The dry residue was then partitioned between $CH_2C_{12}$ and $H_{20}$ to give 4.5 g in organic phase. The aqueous phase was treated with methanol after the water was removed to yield 1.6 g. The organic phases were subjected to flash chromatography on $SiO_2$ using $CH_2Cl_2$—$CH_3OH$ to result in two fractions, I (2.36 g) and II (1.97 g). Reverse phase flash chromatography on BAKERBOND $C_{18}$ using methanol-water on each fraction was followed by HPLC on PARTISIL 10 ODS-3 (22×50; flow rate 10 mL per min).

The fraction I yielded several compounds in different amounts upon purification by HPLC (70% $CH_3CN$—$H_2O$) as follows:

Compound A ($C_{32}H_{43}NO_3$, M.W. 489.3243 (calcd), 489.3226 (found)) of the chemical formula:

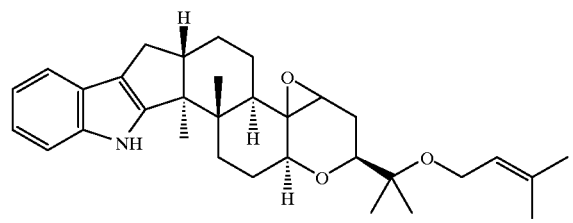

Compound B ($C_{37}H_{51}NO_5$, M.W. 589.3767 (calcd), 589.3749 (found)) of the chemical formula:

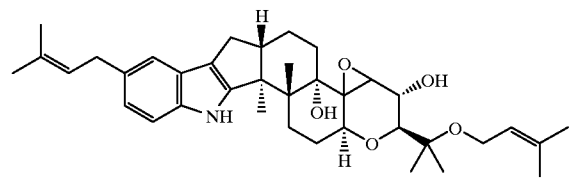

Compound C ($C_{37}H_{47}NO_5$, M.W. 585.3506 (calcd), 585.3454 (found)) of the chemical formula:

Compound C

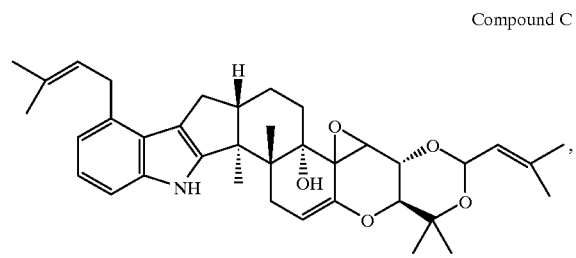

The fraction II provided hydroxypaspalinic acid (Compound D) upon HPLC (50% $CH_3OH$—$H_2O$) and Compound G:

Compound D (29.2 mg; $C_{28}H_{37}NO_5$; M.W. 467.2672 (calcd), 467.2641 (found)) of the chemical formula:

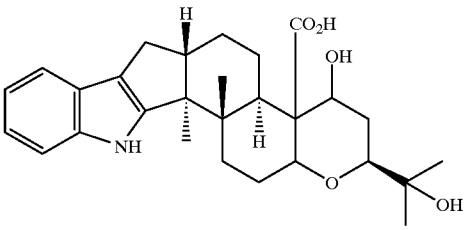

Compound G ($C_{37}H_{49}NO_6$; M.W. 603.3559 (calcd))

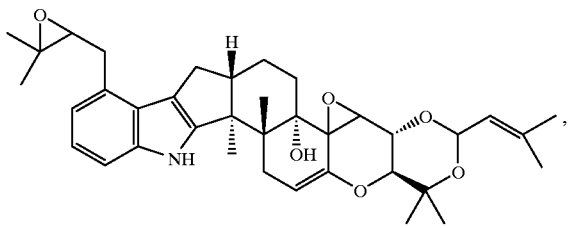

Compound G

$^{13}$C NMR Data $^{13}$C NMR spectra were recorded in $CD_2Cl_2$ and $CD_3OD$ at 125 MHz on Varian Unity 500 NMR spectrometer at 25° C. Chemical shifts are given in ppm relative to tetramethylsilane (TMS) at zero ppm using the solvent peak at 53.8 ($CD_2Cl_2$) and 49.0 ($CD_3OD$) ppm as internal standard.

Compound A ($CD_2Cl_2$): 16.0, 17.9, 18.0, 18.7, 19.2, 21.0, 23.7, 25.77, 25.81, 27.5, 27.7, 28.1, 30.8, 34.8, 42.7, 50.4, 51.0, 58.4, 64.9, 67.5, 69.1, 71.8, 75.3, 78.2, 79.5, 111.1, 117.6, 118.4, 120.8, 121.2, 123.7, 124.6, 132.0, 134.6, 137.4, 140.6, 151.8 ppm. The carbon count of 37 is in agreement with the HR-EIMS derived molecular formula $C_{37}H_{51}NO_5$.

Compound B ($CD_2Cl_2$): 14.6, 16.6, 18.0, 21.3, 22.4, 23.3, 24.5, 25.8, 26.6, 27.5, 29.7, 32.9, 39.8, 41.3, 50.0, 50.7, 56.2, 59.1, 61.8, 73.89, 73.97, 76.0, 111.7, 118.5, 118.6, 119.8, 120.7, 122.9, 125.4, 135.1, 140.3, 150.5 ppm. The carbon count of 32 is in agreement with the HR-EIMS derived molecular formula $C_{32}H_{43}NO_3$.

Compound C ($CD_2Cl_2$): 16.2, 16.8, 18.0, 18.7, 20.1, 20.8, 25.6, 25.8, 28.1, 29.4, 30.8 (2×), 32.3, 44.1, 50.4, 50.7, 60.7, 65.2, 71.4, 73.9, 75.0, 76.6, 93.2, 106.3, 109.5, 117.2, 119.3, 121.2, 122.2, 124.2, 124.9, 132.1, 133.4, 139.8, 140.2, 144.9, 151.3 ppm. The carbon count of 37 is in agreement with the HR-EIMS derived molecular formula $C_{37}H_{47}NO_5$.

Compound D ($CD_3OD$): 14.8, 16.9, 24.7, 25.4, 26.1, 26.2, 26.3, 28.3, 32.3, 33.9, 40.8, 41.5, 50.3, 53.5, 53.7, 68.3, 72.6, 77.6, 79.7, 112.6, 118.0, 118.7, 119.7, 120.7, 126.2, 142.1, 152.1, 178.1 ppm. The carbon count of 28 is in agreement with the HREI-MS derived molecular formula $C_{28}H_{37}NO_5$.
Compound G ($CD_2Cl_2$): 16.0, 16.8, 18.7, 18.9, 19.1, 20.9, 25.0, 25.6, 27.7, 28.35, 28.44, 29.4, 30.7, 33.1, 42.7, 50.6, 50.7, 58.8, 61.5, 64.6, 68.2, 71.4, 71.7, 72.0, 74.9, 78.5, 93.0, 110.2, 117.0, 119.7, 121.1, 122.6, 125.1, 129.6, 139.3, 140.0, 151.9 ppm. The NMR data indicates a carbon count of 37 and a molecular formula $C_{37}H_{47}NO_6$.

$^1$H NMR Data $^1$H NMR spectra were recorded at 500 MHz in $CD_2Cl_2$ Varian XL300 on a Unity 500 NMR spectrometer at 25° C. and in $CD_3OD$ for Compound D at 300 MHz on a Varian XL300 spectrometer at ambient temperature. Chemical shifts are indicated in ppm relative to TMS at zero ppm using the solvent peak at δ5.32 ($CD_2Cl_2$) and 3.30 ($CD_3OD$) as internal standard. Only diagnostic peaks are noted.

Compound A ($CD_2Cl_2$): δ 1.11 (3H, s), 1.22 (3H, s), 1.25 (3H, s), 1.28 (3H, s), 1.66 (3H, br s), 1.73 (3H, br s), 1.74 (6H, br s), 1.91 (1H, m), 2.03 (1H, m), 2.26 (1H, m), 2.36 (1H dd, J=11, 13 Hz), 2.66 (1H, dd, J=6.5, 13 Hz), 2.79 (1H, m), 3.34 (1H, d, J=9 Hz), 3.38 (2H, m), 3.56 (1H, br s), 3.96 (3H, m), 4.17 (1H, t, J=8.5 Hz), 5.26 (1H, m), 5.35 (1H, m), 6.86 (1H, dd, J=1.5, 8 Hz), 7.09 (1H, br s), 7.17 (1H, d, J=8 Hz), 7.74 (1H, br s, NH).

Compound B ($CD_2Cl_2$): δ 1.02 (3H, s), 1.08 (3H, s), 1.11 (3H, s), 1.14 (3H, s), 1.64 (3H, br s), 1.72 (3H, br s), 1.86 (1H, m), 1.94 (1H, m), 2.09 (1H, m), 2.25 (1H, m), 2.37 (1H, dd, J=10.5, 13.5 Hz), 2.68 (1H, dd, J=6.5, 13.5 Hz), 2.79 (1H, m), 3.42 (1H, br d, J=3 Hz), 3.66 (1H, dd, J=2.5, 11 Hz), 3.88 (1H, m), 3.96 (1H, m), 5.25 (1H, m), 5.35 (1H, m), 7.02 (1H, dt, J=1.5, 7 Hz), 7.05 (1H, dt, J=1.5, 7), 7.30 (1H, m), 7.39 (1H, m), 7.88 (1H, br s, NH).

Compound C ($CD_2Cl_2$): δ 1.17 (3H, s), 1.30 (3H, s), 1.31 (3H, s), 1.32 (3H, s), 1.71 (3H, d, J=1.5 Hz), 1.74 (6H, d, J~1 Hz), 1.76 (3H, d, J~1 Hz), 1.67 (1H, m), 1.88 (1H, dd, J=7, 16 Hz), 1.95 (1H, m), 2.57 (1H, dd, J=10.5, 13.0 Hz), 2.77 (1H, m), 2.84 (1H, dd, J=6.5, 13.0 Hz), 3.18 (1H, br d, J~16 Hz), 3.58 (1H, br d, J=7 Hz), 3.86 (1H, s), 3.96 (1H, d, J=10 Hz), 4.00 (1H, d, J=10 Hz), 5.21 (1H, m), 5.35 (1H, m), 5.39 (1H, dd, J=2, 7 Hz), 5.47 (1H, d, J=6.5 Hz), 6.81 (1H, dd, J=1, 7 Hz), 6.96 (1H, dd, J=7, 8 Hz), 7.14 (1H, dd, J=1, 8 Hz), 7.83 (1H, br s, NH).

Compound D ($CD_3OD$ at 300 MHz): δ 1.01 (3H, s), 1.09 (3H, s), 1.12 (3H, s), 1.20 (3H, s), 2.21 (1H, dd, J=4, 12 Hz), 2.29 (1H, dd, J=10.5, 13.0 Hz), 2.61 (1H, dd, J=6.5, 13.0 Hz), ~2.73 (1H, m), 3.64 (1H, dd, J=3, 11 Hz), 3.67 (1H, dd, J=4.5, 12 Hz), 4.37 (1H, t, J=3 Hz), 6.92 (2H, m), 7.27 (2H, m).

Compound G ($CD_2Cl_2$): d 1.15 (3H, s), 1.24 (3H, s), 1.27 (3H, s), 1.28 (3H, s), 1.31 (3H, s), 1.40 (3H, s), 1.71 (3H, d, J=1 Hz), 1.74 (3H, d, J=1 Hz), 1.81 (1H, m), 1.93 (1H, m), 2.27 (1H, m), 2.59 (1H, dd, J=13, 15 Hz), 2.69 (1H, dt, J=5, 13.5 Hz), 2.84 (2H, m), 3.14 (2H, m), 3.16 (1H, m), 3.49 (1H, d, J=9.5 Hz), 3.59 (1H, s), 3.91 (1H, dd, J=1, 9.5 Hz), 4.32 (1H, br t, J~9 Hz), 5.20 (1H, m), 5.50 (1H, d, J=6.5 Hz), 6.87 (1H, dd, J=1, 7.5 Hz), 7.00 (1H, dd, J=7.5, 8 Hz), 7.19 (1H, dd, J=1, 8 Hz), 7.93 (1H, br s, NH).

Abbreviations: s=singlet, d=doublet, q=quartet, br=broad, m=multiplet, J=$^1$H-$^1$H coupling constant in Hertz (±0.5 Hz).

EXAMPLE 2
Preparation of Methyl Hydroxypaspalinate, Compound E

To a methanolic solution of the hydroxypaspalinic acid (Compound D, 7.8 mg, 0.016 mM) was added (trimethylsilyl)diazomethane (($(CH_3)_3SiCHN_2$, 2 M solution in hexanes) in excess. The mixture was stirred at room temperature until the faint yellow color dissipated. The solvent was then removed under nitrogen to give the methyl ester (TLC 5% $CH_3OH$—$CH_2Cl_2$, $R_f$ 0.19 (acid), 0.39 (ester)). It was purified by HPLC on PARTISIL 10 ODS-3 (22×50) using 60% $CH_3CN$—$H_2O$ (flow rate 10 mL per min) to afford methyl hydroxypaspalinate (Compound E; M.W. 481). It was eluted at 149.6 min. and has the following formula:

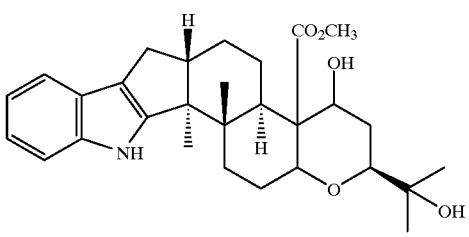

$^{13}$C NMR spectrum was recorded in $CD_3OD$ at 75 MHz on a Varian XL300 NMR spectrometer at ambient temperature. Chemical shifts are given in ppm relative to tetramethylsilane (TMS) at zero ppm using the solvent peak at 49.0 ($CD_3OD$) ppm as internal standard. 14.8, 16.6, 24.6, 25.4, 25.9, 26.0, 26.2, 28.3, 32.5, 33.7, 40.6, 41.6, 50.3, 51.5, 53.7, 53.8, 68.1, 72.6, 77.1, 79.4, 112.6, 118.0, 118.7, 119.7, 120.7, 126.2, 142.1, 151.9, 176.2 ppm. The carbon count of 29 and chemical shift positions are consistent with its assignment as the methyl ester of Compound D.

$^1$H NMR spectrum was recorded at 300 MHz in CD$_3$OD on a Varian XL300 spectrometer at ambient temperature. Chemical shifts are indicated in ppm relative to TMS at zero ppm using the solvent peak at 83.30 (CD$_3$OD) as internal standard. Only diagnostic peaks are noted. δ 0.96 (3H, s), 1.00 (3H, s), 1.12 (3H, s), 1.16 (3H, s), 1.42 (1H, ddd, J=2.5, 12, 14 Hz), 1.91 (2H, m), 2.22 (1H, m), 2.28 (1H, dd, J=10.5, 13.0 Hz), ~2.59 (1H, m), 2.60 (1H, dd, J=6.5, 13.0 Hz), ~2.69 (1H, m), 3.62 (1H, dd, J=2, 12 Hz), 3.65 (3H, s), 3.68 (1H, dd, J=4.0, 12 Hz), 4.35 (1H, t, J=~3 Hz), 6.92 (2H, m), 7.26 (2H, m).

EXAMPLE 3
Synthesis of Paxizoline, Compound F

Crystalline NH$_2$OH.HCl (32 mg, 0.45 mM) was added to a solution of paxilline (20 mg, 0.045 mM) in C$_2$H$_5$OH (2 mL). The mixture was flushed with nitrogen and stirred until the reaction, monitored by TLC (SiO$_2$, 10% CH$_3$OH—CH$_2$Cl$_2$; R$_f$ 0.67 (ketone) and 0.56 (oxime)), was complete. The solvent was removed, then the residue was transferred to a separatory funnel using ether (5 mL). The organic layer was washed consecutively with water (3×1 mL), saturated aqueous NaCl (1×1 mL), then dried with anhydrous MgSO$_4$, filtered through a sintered glass. The solvent was removed in vacuo. The crude mixture was purified by TLC (SiO$_2$ 60 F-254, 5% CH$_3$OH—CH$_2$Cl$_2$) to give paxilline oxime (18.6 mg; C$_{27}$H$_{34}$O$_4$N$_2$, M.W. 450.2518 (calcd), 450.2517 (found)).

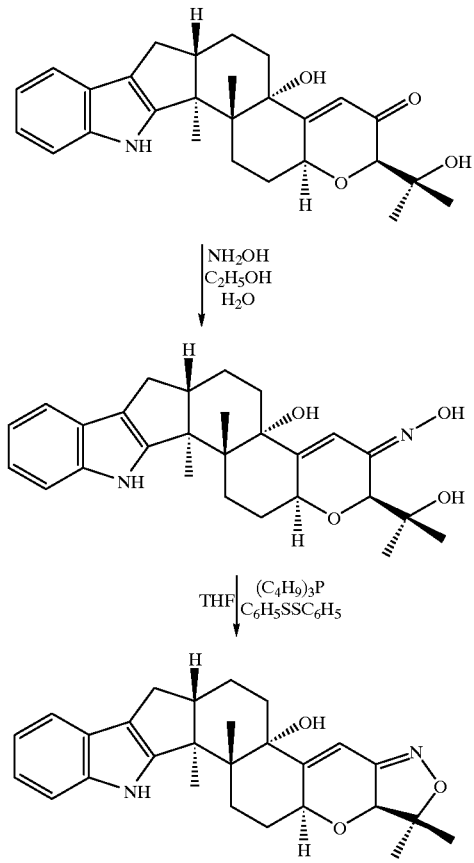

To a mixture of paxilline oxime (10 mg, 0.022 mM) and diphenyl disulfide (4.85 mg, 0.022 mM) in dry tetrahydrofuran (2 mL) was added tributylphosphine (9 mg, 0.044 mM). The mixture was stirred at room temperature overnight under nitrogen, then the solvent was removed. The crude product was purified by HPLC on PARTISIL 10 ODS-3 (9.4×50) using 70% CH$_3$OH—H$_2$O (flow rate 3 mL per min) to give Compound F; 7.5 mg, C$_{27}$H$_{32}$N$_2$O$_3$, M.W. 432.2413 (calcd), 432.2403 (found), UV (CH$_3$OH) λ$_{max}$ (nm) 234, 263, λ$_{min}$ 252).

$^{13}$C NMR(CD$_2$Cl$_2$) 75 MHz on Varian XL300 NMR spectrometer at ambient temperature. Chemical shifts are given in ppm relative to tetramethylsilane (TMS) at zero ppm using the solvent peak at 53.8 (CD$_2$Cl$_2$) ppm as internal standard: 16.3, 19.9, 20.3, 21.3, 25.3, 27.4, 28.5, 28.8, 35.1, 43.3, 50.0, 51.1, 74.9, 78.3, 85.8, 86.2, 109.0, 111.7, 117.5, 118.6, 119.8, 120.7, 125.5, 140.1, 152.4, 154.6, 155.2 ppm. The NMR data indicates a carbon count of 27 consistent with the molecular formula C$_{27}$H$_{32}$N$_2$O$_3$.

$^1$H NMR spectrum was recorded at 300 MHz in CD$_2$Cl$_2$ on a Varian XL300 spectrometer at ambient temperature. Chemical shifts are indicated in ppm relative to TMS at zero ppm using the solvent peak at 65.32 (CD$_2$Cl$_2$) as internal standard. Only diagnostic peaks are noted. δ 1.02 (3H, s), 1.20 (3H, s), 1.33 (3H, s), 1.53 (3H, s), 1.90 (1H, m), 2.24 (1H, m), 2.43 (1H, dd, J=11, 13 Hz), 2.73 (1H, dd, J=6.5, 13 Hz), ~2.74 (1H, m), 2.86 (1H, m), 4.54 (1H, s), 4.87 (1H, ddd, J=2.5, 7, 10 Hz), 6.31 (1H, d, J=2 Hz), 7.03 (2H, m), 7.30 (1H, m), 7.40 (1H, m), 7.86 (1H, br s, NH).

EXAMPLE 4
Electrophysiological Experiments
Methods:

Patch clamp recordings of currents flowing through large-conductance calcium-activated potassium (maxi-K) channels were made from membrane patches excised from cultured bovine aortic smooth muscle cells using conventional techniques (Hamill et al., 1981, Pflügers Archiv. 391, 85–100) at room temperature. Glass capillary tubing (Garner #7052) was pulled in two stages to yield micropipettes with tip diameters of approximately 1–2 microns. Pipettes were typically filled with solutions containing (mM): 150 KCl, 10Hepes (4-(2-hydroxyethyl)-1-piperazine methanesulfonic acid), 1 Mg, 0.01 Ca, and adjusted to pH 7.20 with 3.7 mM KOH. After forming a high resistance (>10$^9$ ohms) seal between the sarcolemmal membrane and the pipette, the pipette was withdrawn from the cell, forming an excised inside-out membrane patch. The patch was excised into a bath solution containing (mM): 150 KCl, 10Hepes, 5 EGTA (ethylene glycol bis(β-aminoethyl ether)-N,N,N',N'-tetraacetic acid), sufficient Ca to yield a free Ca concentration of 1–5 μM, and the pH was adjusted to 7.2 with 10.5 KOH. For example, 4.568 mM Ca was added to give a free concentration of 2 μM at 22° C. An AXOPATCH IC amplifier (Axon Instruments, Foster City, Calif.) with a CV-4 headstage was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2 M KCl. Maxi-K channels were identified by their large single channel conductance (~250 pS) and sensitivity of channel open probability to membrane potential and intracellular calcium concentration.

Data were stored on a RACAL STORE 4DS FM tape recorder (Racal Recorders, Vienna, Va.) or on digital video tape using a video casette recorder after digitizing the signal with VR-10 (Instrutech Corp., Belmont N.Y.) PCM video encoder. The signal was also recorded on chart paper with a GOULD 2400S chart recorder (Gould Inc., Cleveland Ohio). For quantitative analysis, the data was played into a DEC 11-73 (Digital Equipment Corp., Maynard, Mass.) after digitization with a DT2782-8D1A analogue to digital converter (Data Translation Inc., Marlboro, Mass.), or played into a Mac IIx or Quadra 700 computer (Apple Computers) after digitization with an ITC-16 interface (Instrutech Corp., Belmont, N.Y.).

Results:

The effects of the compounds of the present invention on maxi-K channels from bovine aortic smooth muscle were examined in excised inside-out membrane patches. Addition of 10 nM Compound C to the bath produced a rapid and complete block of maxi-K channels that was not reversed during a brief (~10 min) washout. 1 nM of Compound B caused nearly complete block of maxi-K channels suggesting a $K_i$ of less than 1 nM for channel block. Compound D, Compound A and Compound E were weaker blockers of maxi-K channels than Compound C. 10 nM Compound D caused less than a 50% reduction in channel open probability, and complete block was not observed at 1 $\mu$M. 10 nM of Compound A blocked a small fraction of channel activity, 100 nM blocked approximately one half of the channel activity, and 1 $\mu$M blocked nearly all of the channel activity. 1 $\mu$M Compound E had no significant effect on channel open probability, while 10 $\mu$M caused an incomplete block of channel activity slowly increasing over 5–10 minutes. Compound F caused approximately a 50% decrease in channel activity at 10 nM. Compound G at 0.1 nM blocked 82% of channels, at 1 nM blocked 98.6%, and at 10 nm caused >99% block. The data is summarized in the table below:

| COMPOUND | [50% CHANNEL BLOCK] |
| --- | --- |
| A | 100 nm (approx.) |
| B | <1 nM |
| C | <10 nM |
| D | 1 $\mu$M (approx.) |
| E | >10 $\mu$M |
| F | 10 nM (approx.) |
| G | <0.1 nM (approx.) |

EXAMPLE 5

Biochemical Experiments

Methods:

The interaction of [$^{125}$I]ChTX with bovine aortic sarcolemma membrane vesicles was determined under conditions as described (Vazquez et al., 1989, J. Biol. Chem. 264, 20902–20909). Briefly, sarcolemma membrane vesicles were incubated in 12×75 polystyrene tubes with ca. 25 pM [$^{125}$I]ChTX (2200 Ci/mmol), in the absence or presence of test compound, in a media consisting of 20 mM NaCl, 20 mM Tris-HCl pH 7.4, 0.1% bovine serum albumin, 0.1% digitonin. Nonspecific binding was determined in the presence of 10 nM ChTX. Incubations were carried out at room temperature until ligand binding equilibrium is achieved at ca. 90 min. At the end of the incubation period, samples were diluted with 4 mL ice-cold 100 mM NaCl, 20 mM Hepes-Tris pH 7.4 and filtered through GF/C glass fiber filters that have been presoaked in 0.5% polyethylenimine. Filters were rinsed twice with 4 mL ice-cold quench solution. Radioactivity associated with filters was determined in a gamma counter. Specific binding data in the presence of each compound (difference between total binding and nonspecific binding) was assessed relative to an untreated control.

Results:

Compound D (hydroxypaspalinic acid) did not have any effect on binding in the range of concentrations from 1 nM to 100 $\mu$M. Compound E (methylhydroxypaspalinate) did not affect [$^{125}$I]ChTX binding from 1 nM to 100 $\mu$M. Compound A and Compound C inhibited binding by 2% and 29%, respectively, when tested at 10 $\mu$M.

The effect of Compound F, paxizoline, was investigated by increasing the concentration of compound in the assay from 1 nM to 100 $\mu$M. This compound produced two opposite effects on toxin binding. In the range of 50 nM to 2 $\mu$M, there was a small increase in the amount of toxin bound to its receptor. At concentrations above 5 $\mu$M, Compound F caused a concentration-dependent inhibition of binding. It appears that the maximum level of inhibition saturates at ca. 32% control.

Compound G inhibited binding by 35% at 10 $\mu$M.

EXAMPLE 6

The activity of the compounds can also be quantified by the following assays.

A. Maxi-K Channel

The identification of inhibitors of the Maxi-K channel can be accomplished using Aurora Biosciences technology, and is based on the ability of expressed Maxi-K channels to set cellular resting potential after transient transfection of both $\alpha$ and $\beta$ subunits of the channel in TsA-201 cells. In the absence of inhibitors, cells display a hyperpolarized membrane potential, negative inside, close to $E_K$ (−80 mV) which is a consequence of the activity of the Maxi-K channel. Blockade of the Maxi-K channel will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$). Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization.

Transient transfection of the Maxi-K channel in TsA-201 cells can be carried out as previously described (Hanner et al. (1998) J. Biol. Chem. 273, 16289–16296) using FUGENE63 as the transfection reagent. Twenty four hours after transfection, cells are collected in $Ca^{2+}$—$Mg^{2+}$-free Dulbecco's phosphate-buffered saline (D-PBS), subjected to centrifugation, plated onto 96-well poly-d-lysine coated plates at a density of 60,000 cells/well, and incubated overnight. The cells are then washed 1× with D-PBS, and loaded with 100 $\mu$l of 4 $\mu$M $CC_2DMPE$-0.02% pluronic-127 in D-PBS. Cells are incubated at room temperature for 30 min in the dark. Afterwards, cells are washed 2× with D-PBS and loaded with 100 $\mu$l of 6 $\mu$M $DiSBAC_2(3)$ in (mM): 140 NaCl, 0.1 KCl, 2 $CaCl_2$, 1 $MgCl_2$, 20Hepes-NaOH, pH 7.4, 10 glucose. Test compounds are diluted into this solution, and added at the same time. Cells are incubated at room temperature for 30 min in the dark.

Plates are loaded into a voltage/ion probe reader (VIPR) instrument, and the fluorescence emission of both $CC_2DMPE$ and $DiSBAC_2(3)$ are recorded for 10 sec. At this point, 100 $\mu$l of high-potassium solution (mM): 140 KCl, 2 $CaCl_2$, 1 $MgCl_2$, 20Hepes-KOH, pH 7.4, 10 glucose are added and the fluorescence emission of both dyes recorded for an additional 10 sec. The ratio CC$_2$DMPE/DiSBAC$_2$(3), before addition of high-potassium solution equals 1. In the absence of any inhibitor, the ratio after addition of high-potassium solution varies between 1.65–2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

B. Electrophysiological Assays of Compound Effects on High-Conductance Calcium-Activated Potassium Channels Human Non-Pigmented Ciliary Epithelial Cells The activity of high-conductance calcium-activated potassium (maxi-K) channels in human non-pigmented ciliary epithelial cells can be determined using electrophysiological methods. Currents through maxi-K channels can be recorded in the inside-out configuration of the patch clamp technique, where the pipette solution faces the extracellular side of the channel and the bath solution faces the intracellular side. Excised patches contain one to about fifty maxi-K channels. Maxi-K channels can be identified by their large single channel conductance (250–300 pS), and by sensitivity of channel gating to membrane potential and intracellular calcium concentration. Membrane currents are recorded using standard electrophysiological techniques. Glass pipettes (Garner 7052) are pulled in two stages with a Kopf puller (model 750), and electrode resistance is 1–3 megohms when filled with saline. Membrane currents are recorded with EPC9 (HEKA Instruments) or Axopatch 1D (Axon Instruments) amplifiers, and digital conversion was done with ITC-16 interfaces (Instrutech Corp). Pipettes are filled with (mM); 150 KCl, 10Hepes, 1 MgCl$_2$, 0.01 CaCl$_2$, 3.65 KOH, pH 7.20. The bath (intracellular) solution is identical, except, in some cases, calcium is removed, 1 mM EGTA is added and mM KCl is replaced with 20 mM KF to eliminate calcium to test for calcium sensitivity of channel gating. Drugs are applied to the intracellular side of the channel by bath perfusion.

Human non-pigmented ciliary epithelial cells can be grown in tissue culture as described (Martin-Vasallo, P., Ghosh, S., and Coca-Prados, M., 1989, J. Cell. Physiol. 141, 243–252), and plated onto glass cover slips prior to use. High resistance seals (>1 Gohm) are formed between the pipette and cell surface, and inside out patches are excised. Maxi-K channels in the patch are identified by their gating properties; channel open probability increases in response to membrane depolarization and elevated intracellular calcium. In patches used for pharmacological analysis, removing intracellular calcium eliminates voltage-gated currents. Maxi-K currents are measured after depolarizing voltage steps or ramps that cause channel opening.

What is claimed is:

1. A method for treating ocular hypertension or glaucoma which comprises administering to a patient in need of such treatment a therapeutically effective amount of a compound of Formula I:

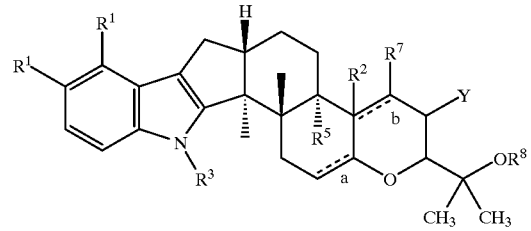

(I)

or a pharmaceutically acceptable salt, enantiomer, diastereomer or mixture thereof: wherein, R$^1$ is:
 (a) H,
 (b) 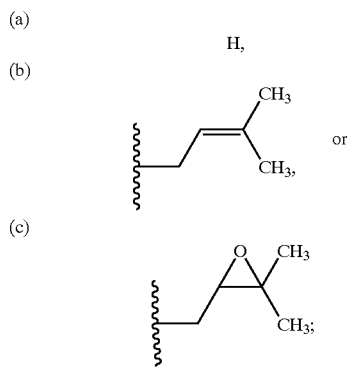
 or
 (c)

R$^2$ is:
 (a) CO$_2$C$_{1-6}$alkyl,
 (b) H,
 (c) OH, or
 R$^2$ and R$^7$ are taken together to form an oxirane ring when b is a single bond;

R$^3$ is:
 (a) H, or
 (b) (C=O)OC$_{1-6}$alkyl;

R$^5$ is:
 (a) H,
 (b) OH, or
 (c) OC$_{1-6}$alkyl;

R$^7$ is H, OC$_{1-6}$ alkyl or R$^7$ and R$^2$ are taken together to form an oxirane ring when b is a single bond;

Y is:
 (a) H,
 (b) OH,
 (c) OC$_{1-6}$alkyl,
 or Y and R$^8$ are joined such that one of the following rings is formed:

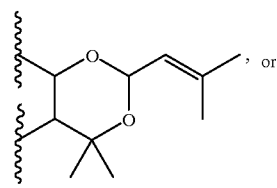, or (1)

(2)

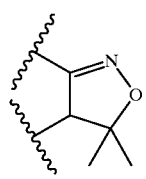

$R_8$ is $C_{1-10}$ alkyl or $C_{2-10}$ alkenyl; and

_____ is a double bond optionally present at a or b or at both a and b.

2. The method according to claim 1 wherein the compound of formula I is applied as a topical formulation.

3. The method of claim 1, wherein the compound is selected from:

(a)

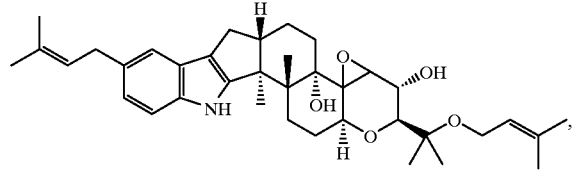

(b)

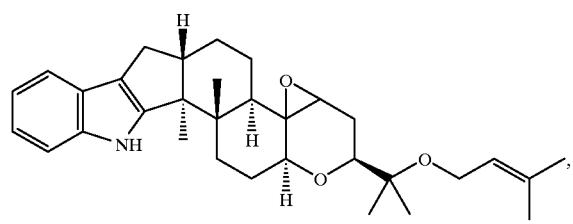

(c)

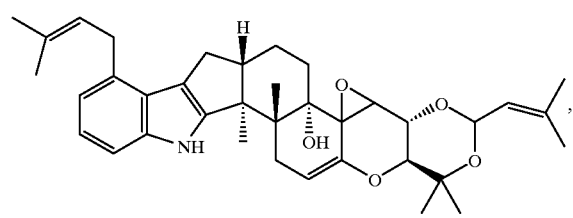

(d)

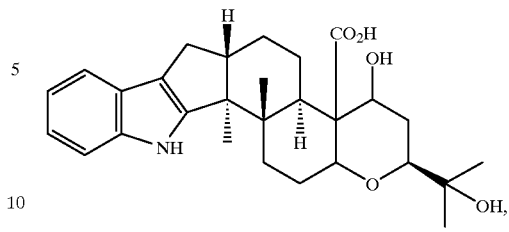

(e)

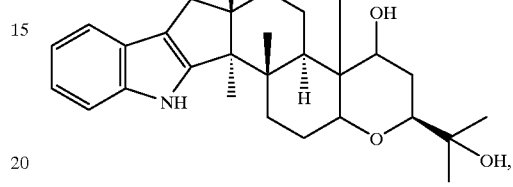

(f)

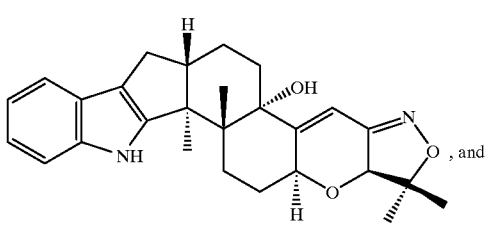

, and (g)

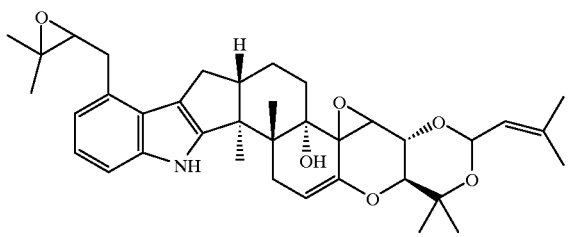

and pharmaceutically acceptable salts, enantiomers, diastereomers and mixtures thereof.

4. The method according to claim 2 wherein the topical formulation is a solution or suspension.

* * * * *